United States Patent
Thacker et al.

(10) Patent No.: US 7,657,317 B2
(45) Date of Patent: Feb. 2, 2010

(54) EVALUATING STIMULATION THERAPIES AND PATIENT SATISFACTION

(75) Inventors: James R. Thacker, Eureka, MO (US); Carla M. Woods, Beverly Hills, CA (US); Sridhar Kothandaraman, Valencia, CA (US); John D. H. King, Los Angeles, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 474 days.

(21) Appl. No.: 11/115,789

(22) Filed: Apr. 26, 2005

(65) Prior Publication Data

US 2006/0241722 A1    Oct. 26, 2006

(51) Int. Cl.
*A61N 1/36* (2006.01)
(52) U.S. Cl. .......................................... 607/46
(58) Field of Classification Search ................... 607/46, 607/48, 52, 58
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,232,679 A | 11/1980 | Schulman | |
| 4,793,353 A | 12/1988 | Borkan | |
| 5,443,486 A | 8/1995 | Hrdlicka et al. | |
| 5,653,739 A | 8/1997 | Maurer et al. | |
| 5,893,883 A | 4/1999 | Torgerson et al. | |
| 5,938,690 A | 8/1999 | Law et al. | |
| 6,027,456 A | 2/2000 | Feler et al. | |
| 6,052,624 A | 4/2000 | Mann | |
| 6,120,467 A | 9/2000 | Schallhorn | |
| 6,249,703 B1 | 6/2001 | Stanton et al. | |
| 6,308,102 B1 | 10/2001 | Sieracki et al. | |
| 6,381,496 B1 | 4/2002 | Meadows et al. | |
| 6,393,325 B1 | 5/2002 | Mann et al. | |
| 6,440,090 B1 | 8/2002 | Schallhorn | |
| 6,516,227 B1 | 2/2003 | Meadows et al. | |
| 6,587,724 B2 | 7/2003 | Mann | |
| 6,609,031 B1 | 8/2003 | Law et al. | |
| 6,622,048 B1 | 9/2003 | Mann et al. | |
| 6,675,049 B2 | 1/2004 | Thompson et al. | |
| 6,687,538 B1 | 2/2004 | Hrdlicka et al. | |
| 6,735,475 B1 * | 5/2004 | Whitehurst et al. | ........... 607/46 |
| 6,748,276 B1 | 6/2004 | Daignault, Jr. et al. | |
| 7,167,743 B2 * | 1/2007 | Heruth et al. | ............... 600/509 |
| 2003/0114899 A1 | 6/2003 | Woods et al. | |
| 2003/0153959 A1 | 8/2003 | Thacker et al. | |
| 2003/0171789 A1 | 9/2003 | Malek et al. | |

(Continued)

FOREIGN PATENT DOCUMENTS

EP    0 811 395 A2    12/1997

(Continued)

*Primary Examiner*—George R Evanisko
*Assistant Examiner*—Amanda Patton
(74) *Attorney, Agent, or Firm*—Vista IP Law Group LLP

(57) ABSTRACT

A tissue stimulation system is provided that evaluates and/or scores stimulation sets based on both patient feedback and frequency of use. Stimulation sets and any associated scores and/or usage may be stored in a retrievable database. Upon subsequent stimulation sessions, a patient may select stimulation sets that have a high score and/or usage in order to effectively meet therapeutic objectives. Methods of determining patient satisfaction, which involve evaluating patient pain before and after stimulation pulses are applied, are also provided herein.

16 Claims, 3 Drawing Sheets

U.S. PATENT DOCUMENTS

| | | |
|---|---|---|
| 2003/0177031 A1 | 9/2003 | Malek |
| 2003/0195591 A1 | 10/2003 | Law et al. |
| 2004/0098063 A1 | 5/2004 | Goetz |
| 2004/0138516 A1 | 7/2004 | Osorio et al. |
| 2004/0143302 A1 | 7/2004 | Sieracki et al. |
| 2004/0158119 A1 | 8/2004 | Osorio et al. |
| 2004/0158298 A1 | 8/2004 | Gliner et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkoski |
| 2004/0215288 A1 | 10/2004 | Lee et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0209644 A1 * | 9/2005 | Heruth et al. ............... 607/3 |
| 2005/0209655 A1 | 9/2005 | Bradley et al. |

FOREIGN PATENT DOCUMENTS

| | | |
|---|---|---|
| WO | WO 01/39831 A1 | 6/2001 |
| WO | WO 2004/041353 A1 | 5/2004 |
| WO | WO 2004/093984 A1 | 11/2004 |

* cited by examiner

EVALUATING STIMULATION THERAPIES AND PATIENT SATISFACTION

BACKGROUND OF THE INVENTION

The present invention relates to tissue stimulation systems and more particularly to evaluating stimulation therapies and patient satisfaction with stimulation therapies.

One example of a stimulation system is a spinal cord stimulation system ("SCS"). Spinal cord stimulation is a well accepted clinical method for reducing pain in certain populations of patients. An SCS system typically includes an Implantable Pulse Generator (IPG) or a radio-frequency (RF) transmitter and receiver, electrodes, electrode leads, and when necessary, lead extensions. The electrodes are implanted along the dura of the spinal cord, and the IPG or RF transmitter generates electrical pulses that are delivered, through the electrodes, to the dorsal column and dorsal root fibers within the spinal cord. Individual electrode contacts (the "electrodes") are arranged in a desired pattern and spacing in order to create an electrode array. Individual wires within one or more electrode leads connect with each electrode in the array. The electrode leads exit the spinal column and attach to one or more electrode lead extensions, when necessary. The electrode leads or extensions are typically tunneled around the torso of the patient to a subcutaneous pocket where the IPG or RF-receiver is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical impulses to a plurality of electrodes. As another example, U.S. Pat. No. 3,724,467 issued Apr. 3, 1973 for "Electrode Implant For The Neuro-Stimulation of the Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes, which are positioned longitudinally on the spinal cord. Electrical pulses applied to the electrodes block perceived intractable pain, while allowing passage of other sensations. A patient operated switch allows the patient to adjust the stimulation parameters.

An SCS system treats chronic pain by providing electrical stimulation pulses through the electrodes of an electrode array located at the distal end of a lead placed epidurally next to a patient's spinal cord. The combination of electrodes used to deliver stimulation pulses to the targeted tissue constitutes an electrode configuration. In other words, an electrode configuration represents the polarity, being positive, negative, or zero, and for certain SCS systems with such capabilities, relative percentage of the current or voltage provided through each of the electrodes. Electrode arrays used with known SCS systems may employ between 1 and 16 electrodes on a lead. Electrodes are selectively programmed to act as anodes, cathodes, or left off, creating an electrode configuration. The number of electrodes available, combined with the ability to generate a variety of complex stimulation pulses, presents a huge selection of electrode configurations and stimulation parameters (together referred to herein as "stimulation sets") to the clinician. When an SCS system is implanted, a procedure is performed to select one or more effective stimulation sets for a particular patient. Such a session of applying various stimulation parameters and electrode configurations may be referred to as a "fitting" or "programming" session. Additionally, a series of electrode configurations to be applied to a patient may be organized in a steering table or in another suitable manner.

Other parameters that may be controlled or varied in SCS are the frequency of pulses provided through the electrode array, pulse width, and the strength (amplitude) of pulses delivered. Amplitude may be measured in milliamps, volts, etc., as appropriate, depending on whether the system provides stimulation from current sources or voltage sources. With some SCS systems, the distribution of the current/voltage across the electrodes (including the case of the pulse generator or receiver, which may act as an electrode) may be varied such that the current is supplied via numerous different electrode configurations. In different configurations, different combinations of electrodes may provide current (or voltage) in different relative percentages of positive and negative current (or voltage). Moreover, there may be some electrodes that remain inactive for certain electrode configurations, meaning that no current is applied through the inactive electrode.

Therefore, an "electrode configuration" refers to a polarity and/or to a relative distribution of current or relative magnitude of voltage applied through the electrodes of the electrode array. Electrodes may be positive, negative, or turned off, such that a subset of anodes and cathodes are created within the electrode array. A polarity of each electrode may be a positive or negative "1" or a fraction thereof. For example, one electrode of the electrode array may have a polarity of negative "1" (cathode), while another electrode may have a polarity of positive "1" (anode).

Alternatively, a polarity may be spread out among different electrodes, for example, such that one electrode has a polarity of +0.75, while the other electrode(s) have +0.25. This distribution is known as polarity "distribution" or "percentage" among the electrodes of an electrode array. In the above examples, if an electrode has a polarity of negative 1, it is a cathode with 100% of the negative polarity distribution. If an electrode has a polarity of +0.75, it is an anode with 75% of the polarity distribution (with one or more additional electrodes accounting for the remaining 25% of the positive polarity distribution). Thus, a numerical value may be easily associated with a polarity distribution. In the case of current-controlled electrodes, in this example 75% of the anodic current would emanate from the first anode and 25% of the anodic current from the remaining anode(s). In the case of voltage-controlled electrodes, in this example the voltage magnitude of the first anode (e.g. +3.0 volts or 75%) would be three times that of the other anode(s) (+1.0 volts or 25%). The electrode configuration, along with pulse frequency, pulse width, and pulse amplitude of the voltage/current applied to the selected electrodes may be referred to as a stimulation set.

In order to test the effectiveness on a particular patient of various stimulation parameters and electrode configurations (i.e., parameters sets), it is necessary to provide a series of stimulation parameters in a systematic method. Several such systems exist including the systems disclosed in U.S. Pat. No. 6,393,325, incorporated herein by reference in its entirety, wherein a patient may direct the movement of the stimulus current through a suitable interface. Another method of testing the effectiveness of various stimulation parameters is disclosed in U.S. application Ser. No. 11/026,859, incorporated herein by reference in its entirety. In this Application, during a fitting session with a patient, a clinician uses navigation with two parameter tables to step through and optimize stimulation parameters.

In tissue stimulation applications, various stimulation sets may change the character and success of the patient's experience with the therapy. It would be useful to the clinician to be able to quickly determine the patient's satisfaction with a particular stimulation set for both clinical tracking as well as future programming and adjustment to the stimulation therapy. In previous tissue stimulation systems, patients may have been asked to evaluate the effectiveness of the various stimulation sets that are applied. While the clinician may have sought patient feedback in past systems, a system of evaluating stimulation sets, including evaluations that are not based on memory but are based on more quantitative data, scoring stimulation sets and organizing patient satisfaction is needed.

What is needed is method of creating a patient database including tested stimulation sets and associated feedback on these stimulation sets. Once created, this database may be used in future stimulation sessions, in order to provide the most effective stimulation sets to the patient to meet therapeutic objectives. Additionally, there is a need for evaluating the stimulation set based on patient feedback and/or on frequency of use. Additionally, there is a need for a way to evaluate patient-experienced pain both before and after stimulation pulses are applied to the patient. The associated pain level should be stored in the database in addition to the other patient feedback on the tested stimulation sets.

SUMMARY OF THE INVENTION

Embodiments of the present invention describe a tissue stimulation system and devices and methods for programming the stimulation system. The stimulation system may have an implant device comprising an implantable pulse generator having an implantable electrode array connected thereto, the implantable pulse generator having electrical circuitry therein that generates electrical stimulation pulses. This invention is also applicable to a system having an external transmitter that transmits the energy for pulses to an implanted receiver that receives the energy for the pulses and sends the pulses to the electrodes implanted adjacent the tissue to be stimulated.

One embodiment is a tissue stimulation system comprising: (1) a pulse generating device for generating electrical stimulation pulses, wherein the electrical stimulation pulses are defined by a stimulation set; (2) at least one implanted electrode for delivering the electrical stimulation pulses generated by the pulse generating device; (3) a database which stores one or more stimulation sets and an associated frequency of use for each of the stimulation sets; (4) means for selecting a stimulation set from the database; and (5) a programmer capable of communicating with the pulse generating device in order to program the pulse generating device to generate electrical stimulation pulses in accordance with the selected stimulation set.

The database of the stimulation system may store patient information, clinic information, and tissue stimulation device information. A level of patient satisfaction before and after the stimulation pulses are applied to the patient may be recorded in the database. The database may also store any associated patient feedback with the stimulation sets. Patient feedback may be generated using an interactive display screen. A visual analog scale may be used to evaluate the stimulation sets. Patients may also provide verbal feedback. Objective criteria such as perspiration, muscle tension, respiration rate, heart rate may be used to evaluate stimulation sets and thus generate a score for the set. A score may be calculated for the stimulation set based on one or more of frequency of use and patient feedback.

Another embodiment is a method of evaluating stimulation sets comprising: (1) applying electrical stimulation pulses to a patient, wherein the electrical stimulation pulses are generated by a pulse generating device and are defined by at least one stimulation set; (2) determining a frequency of use for each applied stimulation set; and (3) retrievably storing the frequency and the associated stimulation sets in a database.

The database may be used to select stimulation sets for future stimulation sessions. An updatable score may be calculated for each stimulation set based on both frequency of use and patient feedback. The database may be updated based on frequency of use. Patient feedback may be generated using, e.g., a visual analog scale.

Another embodiment is a method of determining patient satisfaction with a stimulation set, the method comprising: (1) determining a patient's level of pain before applying electrical stimulation pulses to a patient; (2) applying electrical stimulation pulses to the patient, wherein the electrical stimulation pulses are generated by a pulse generating device and are defined by at least one stimulation set; (3) evaluating the applied stimulation sets, wherein the evaluation includes determining the patient's level of pain after applying the electrical stimulation pulses and determining a frequency of use for each applied stimulation set; and (4) retrievably storing the evaluation and the associated stimulation sets in a database.

The levels of pain may be determined using a visual analog scale. A score may be generated for each stimulation set with the following equation:

$$\text{score} = (10 - VAS) + (\text{use percentage}/10),$$

wherein VAS is a value from 1 to 10 indicating a level of pain experienced while the electrical stimulation pulses are applied according to the stimulation set, and wherein the use percentage is a value representing frequency of use for the stimulation set. This score may be stored in the database with the associated stimulation set.

BRIEF DESCRIPTION OF THE DRAWINGS

The above and other aspects of the present invention will be more apparent from the following more particular description thereof, presented in conjunction with the following drawings wherein.

DETAILED DESCRIPTION OF THE INVENTION

It is to be understood that this invention is not limited to the particular devices, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to an "electrode" is a reference to one or more electrodes and equivalents thereof known to those skilled in the art, and so forth. Unless defined otherwise, all technical and scientific terms used herein have the same meanings as commonly understood by one of ordinary skill in the art. Although any methods, devices, and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

The various components of an exemplary SCS system may include an implantable pulse generator (IPG) and programmer used with such system. Implantable components may include an implantable pulse generator, one or more electrode arrays, and (as needed) one or more extensions to connect the array(s) to the IPG. Such implantable components, external devices and circuitry are more fully described in U.S. Pat. No. 6,622,048. Alternatively, a system comprised of an implanted RF receiver and external transmitter, as a pulse generating device in place of an IPG, may be used.

A programming system may include, as described in U.S. Pat. No. 6,622,048, a clinician programmer coupled to a directional device. The clinician programmer typically interfaces with a patient hand-held programmer (HHP) in communicating with the implanted pulse generator. However, other types of communication links between the clinician programmer (i.e., the programming computer) and the IPG may be utilized. Programmers may be in the form of a conventional PC, a laptop, a PDA, a monitor, a hand-held device, and any other suitable computing means.

The electrical stimulation pulses applied to a patient are defined by a stimulation set, comprising an electrode configuration and pulse stimulation parameters.

Figure 1:
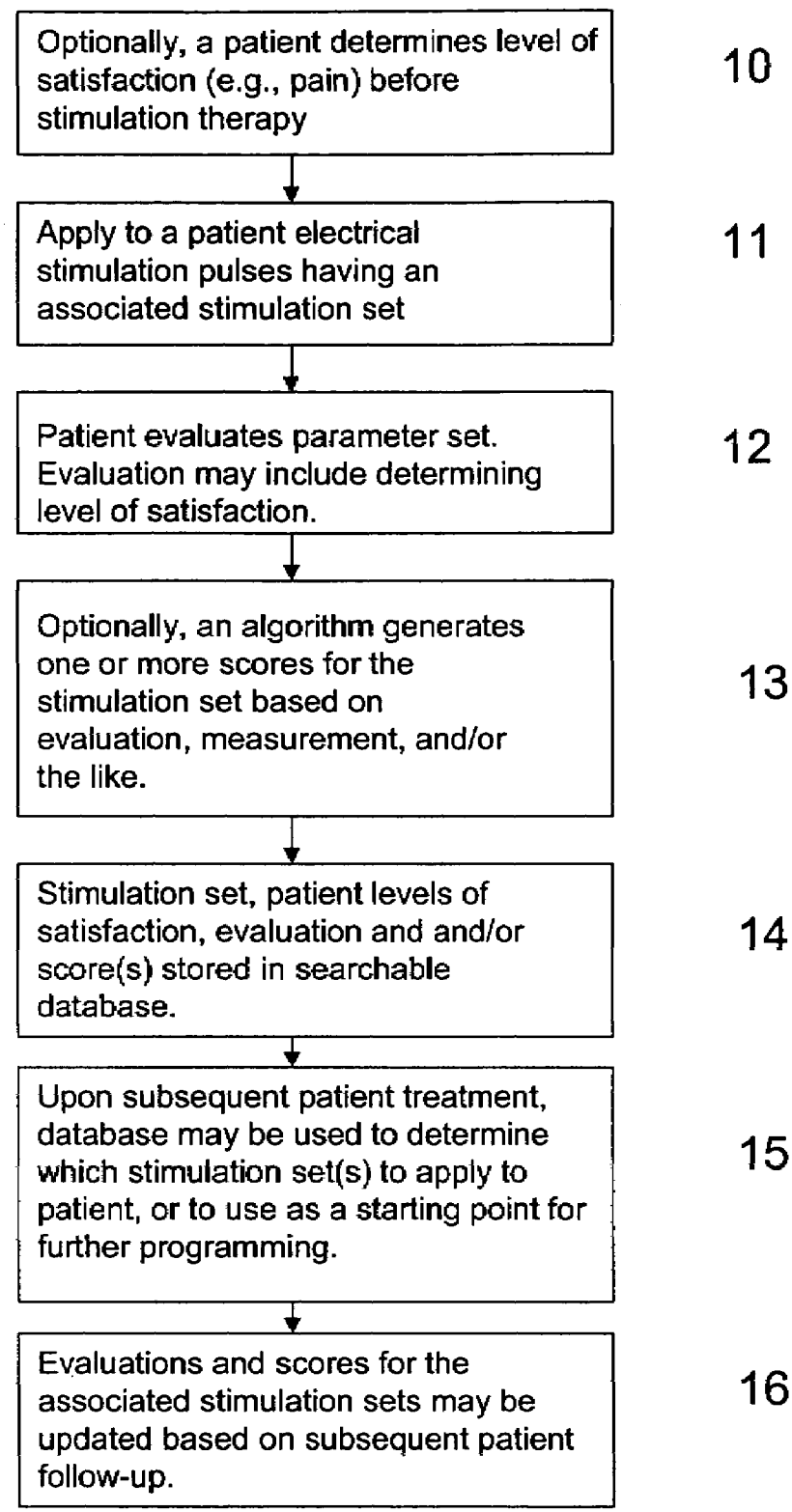
FIG. 1 depicts a flow chart according to one embodiment of the present invention.

A flow chart representing one embodiment of a method of recording, evaluating, scoring, storing, and retrieving stimulation sets and their use is depicted in FIG. 1. As seen in step 10, a first level of patient satisfaction may be determined before any stimulation pulses are applied. Determining patient satisfaction, such as a level of pain, in the absence of stimulation therapies provides a baseline for interpreting patient feedback after stimulation pulses are applied, but this is an optional step. In step 11, a stimulation session is commenced, wherein electrical stimulation pulses are applied to a patient. A stimulation session may be a programming or therapeutic session.

Applied electrical stimulation pulses are evaluated for therapeutic effectiveness at step 12. Many types of evaluations exist, such as verbal communications or a numerical ranking. A clinician, patient, and/or program may evaluate the stimulation set. In patient evaluation, for example, the patient may be prompted to answer questions in order to evaluate the stimulation sets. These patient comments may be recorded to a computer database. Such questioning may be oral or may be automated using a suitable user interface.

In another patient evaluation, the patient may be asked to rank the associated stimulation set while the stimulation pulses are being applied to the patient, using a discrete scale, such as A-F. Alternatively, stimulation sets may be evaluated by the user after a fitting or programming session, wherein a batch of stimulation sets has been tested on a patient. Stimulation sets may be scored according to objective criteria. Objective criteria include measurements of various physiological parameters of the patient, such as perspiration, muscle tension, respiration rate, heart rate, and the like.

Evaluation information may take into account pre-treatment and post-treatment patient information. Determining patient satisfaction in the absence of stimulation therapies provides a baseline for interpreting patient feedback after stimulation pulses are applied. For example, a patient may be asked to identify a level of patient satisfaction or well-being before the stimulation session begins. After stimulation pulses have been applied to the patient, his/her satisfaction level may be determined again. The change in patient satisfaction, if any, may be used to evaluate specific stimulation sets.

Patient satisfaction is commonly represented by a reduction in the sensation of pain. Therefore, a patient may be prompted to select a pain level experienced in the absence of stimulation, a pain level while various stimulation sets are applied, and a pain level after stimulation sets have been applied.

Pain levels or other patient sensations may be evaluated by a patient using a discrete scale, such as 1-10, or A-F, etc. These scales may be incorporated visually into a suitable user interface. Interfaces may include, but are not limited to, display screens, handheld devices, monitors, laptops, and PDAs. The interfaces may be interactive, such as a touch screen. The user may use a mouse, joystick, or stylus for in connection with the interface for the input of patient feedback.

Figure 2:
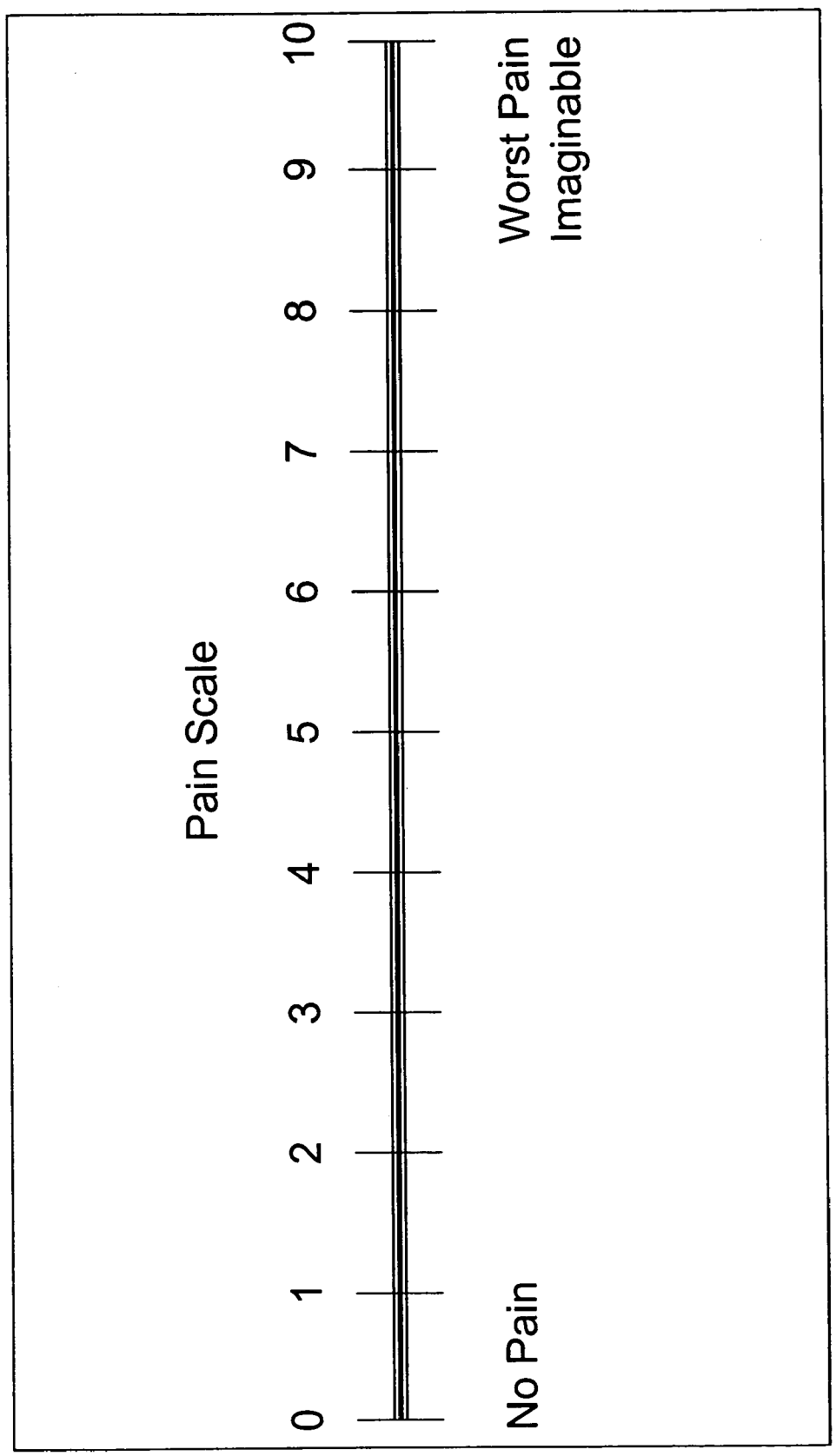
FIG. 2 depicts a display screen comprising a visual analog scale.

An example of one such user interface would be a display screen incorporating a graphical display of a visually continuous scale. A user would be prompted to identify along the continuum a ranking associated with a particular level of satisfaction. For example, a visual analog scale ("VAS"), such as the one depicted in FIG. 2 may be used to determine patient pain levels. The VAS is a 0-10 rating scale, wherein a patient ranks his/her sensation of pain, with "0" being "no pain" and "10" being "the worst pain imaginable." A software application may be used that displays the VAS to the patient, which display may including gradations for each integer on the scale, interpretive cartoons at various levels that characterize the face of a pain sufferer, and/or other indicators to assist patients in evaluating their level of pain. For example, as seen in FIG. 2, each integer along the 0-10 scale is marked and the endpoints of the scale include the pain sensation language. The patient marks the VAS at a spot corresponding to his/her associated level of pain. The software interprets this spot and converts it to a numerical value by counting the pixels from one end of the scale to the patient's marking along the scale and determining the relative score between the two ends of the scale. This software may round or truncate the relative score based on the patient's mark along the continuum to any desired resolution.

Once evaluations have been collected for a stimulation set, a score may be generated for each stimulation set at step 13 in FIG. 1. Various algorithms and programs may be used to convert raw patient feedback into a discrete score for the stimulation set. A score may be computed separately for each measure of feedback, such as a VAS score, a percentage of use score, a heart rate score, and the like. Alternatively, a score may reflect a combination of all the collected feedback, weighting certain criteria more heavily than others. For example, an algorithm may sum together a patient ranking, such as the VAS score, with a less heavily weighted heart rate ranking to obtain a "total" score for the stimulation set. One or more evaluations may thus be used to generate one or more scores for each stimulation set.

A score for a particular stimulation set may also be indicative of its frequency of use. This frequency of use may be patient-specific or may be grouped according to clinic location, according to specific patients having similar diseases or conditions, or across any number of patients. If a patient uses particular stimulation set(s) a majority of the time in his/her therapy sessions, this use percentage is likely indicative of the effectiveness of this stimulation therapy. This use percentage may be used to generate a score for the stimulation sets—the more frequently used stimulation sets having higher scores. Frequency of use may be a separate score for each stimulation set. Alternatively, the frequency of use may also be weighted according to any algorithm to obtain a total score for each stimulation set.

In addition to scoring the stimulation sets by frequency of use, patient feedback may be used to score the stimulation sets. For example, a VAS or some other means of determining a score for the stimulation set from patent feedback may be used alone, or in combination with other factors to generate a total score for the stimulation set. One example of creating a total score for a stimulation set would be to sum together the VAS score with the percentage of use. VAS score is inversely proportional to patient well-being, while percentage of use is directly proportional. Therefore, one simple algorithm for generating a score for a stimulation set is:

total score=(10−VAS)+(use percentage/10), wherein a maximum score a stimulation set may have is 20.

For example, if a stimulation set has a VAS score of 4 and a percentage use of 10%, then a combined total score would be "7" (6+10/10). But if a stimulation set has a VAS score of 7 and a percentage use of 10%, then a combined total score would be "4" (3+10/10). Therefore, the higher the total score, the better the stimulation set. Other algorithms may also be used.

Since a score may be proportional to percentage of use, means for tracking the percentage of use for each stimulation set during therapy sessions and a means for updating the score based on this tracking may be useful. This tracking may be accomplished with any suitable database or software. Again, this tracking of percentage of use may be patient-specific or may be grouped according to patient groups.

Once evaluated, patient feedback and the associated stimulation set may be organized and stored in an appropriate database at step 14. The database may store the stimulation sets and patient feedback, including verbal comments and VAS score. Additionally, the database may store the one or more scores determined for each stimulation set. This score may be indicative of one or more of the patient feedback and the frequency of use. The database may also include patient satisfaction information in the absence of stimulation therapy. As explained above, the patient's sensation of pain before stimulation provides a baseline for determining the effectiveness of the stimulation therapy. Finally, the database may include information regarding patient satisfaction after specific therapies have been applied.

Therefore, stimulation sets may be tracked, scored, stored, organized, updated, and retrievable for each patient. Such organization may be through any suitable computer system, employing, for example, any suitable memory device, computation device, database, user interface, communication connections and/or software. In such a manner, a patient's satisfaction with stimulation sets may be tracked over various stimulation treatment sessions. Various reports may be generated from the described database, including patient satisfaction reports generated over a period of time.

Figure 1A:
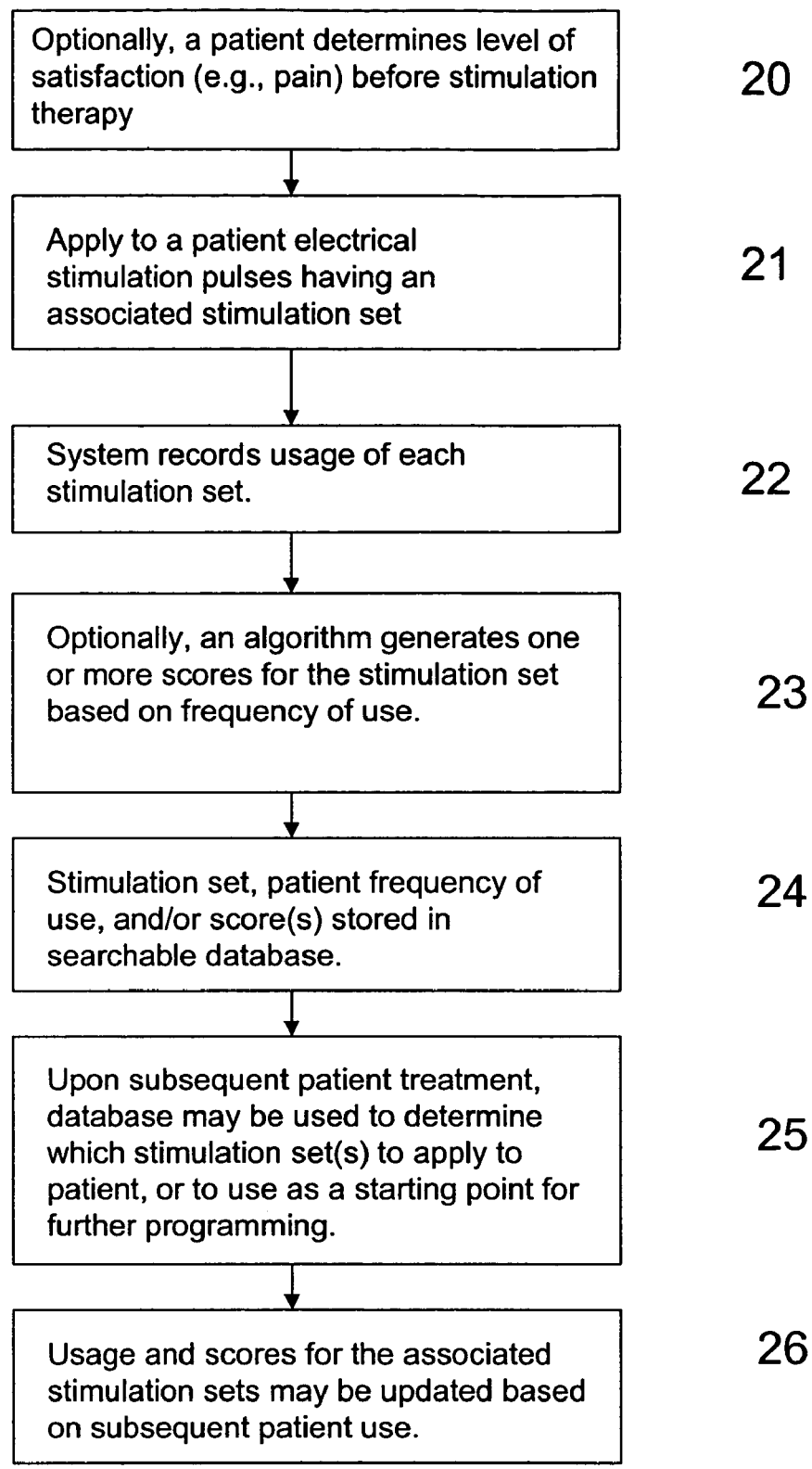
FIG. 1A depicts a flow chart according to one embodiment of the present invention.

By storing the score and/or usage associated with stimulation sets, this score and/or usage is easily retrieved from the database upon subsequent patient follow-ups at step 15 in FIG. 1 (or step 25 in FIG. 1A). Upon subsequent stimulation sessions, the score and/or usage associated with each stimulation set may be used to prioritize the application of preferred stimulation sets. Additionally, the use of the score and/or usage allows the clinician to search for additional stimulation sets if the previously used sets are not meeting the needs of the patient. The score/usage allows a clinician to use a database search tool (either manual or automatic) to request from the database stimulation sets with a score/usage greater than some threshold value. For example, the user may only select stimulation sets that have a total score of 6 or greater or usage of 20% or greater. Alternatively, this threshold may be based on VAS score. For example, the user may select stimulation sets having a VAS score of 5 or lower.

As another example, a stimulation set may initially be found to have a VAS score of 4. Upon presentation at follow-up, the patient may rank this same stimulation set as having a VAS score of 6. The system, recognizing this difference in patient evaluation from day-to-day, may then select different stimulation sets that have a VAS score of less than 6 for use.

The evaluation information may be used to create a patient profile, which may be retrievable from a database and used for each stimulation session. Patient satisfaction information, such as a VAS score in the absence of therapy, may be included in the profile. Other recorded information may also include general information and information related to specific therapy sessions. Such information may include the stimulation sets applied to the patient, including any identified bounds or preferred parameters, any scoring of these parameters, the date, the patient information, the clinic, the attending clinician, the stimulator hardware used, and any other information related to the patient, stimulation and therapy.

During an initial programming session or at subsequent sessions, the stimulation sets may be displayed to the user along with any associated feedback, scores, and/or usage. The graphical displays may be used in any phase of a stimulation session to convey stimulation parameters to a user. The VAS, scores, usage, and/or total scores may be readily displayed to the patient to ease selection of effective stimulation parameters. Alternatively, during evaluation, the patient may not be able to see previous scores/usage for a particular stimulation set, allowing for objective evaluation.

Upon subsequent patient evaluation sessions, the database tracks any changes to the stimulation set scores/usage, at step 16 in FIG. 1. Additionally, evaluation information may be updated within the database based on subsequent use. Since one or more scores, such as total scores, may be proportional to percentage of use, means for tracking the percentage of use for each stimulation set and a means for updating the scores based on the usage may be accomplished with any suitable database or software.

FIG. 1 contemplates an overall patient satisfaction system, wherein patient evaluation of stimulation sets may include a level of satisfaction with a VAS, objective physical measurements, frequency of use, and other suitable evaluations. FIG. 1A represents a specific methodology, wherein the system evaluates the stimulation sets based on the frequency of use. Steps 10 and 11 of FIG. 1 are the same as steps 20 and 21 of FIG. 1A: a patient level of satisfaction before the stimulation is applied may be determined and electrical stimulation pulses are applied to the patient. At step 22, the system records usage data for each stimulation set. At step 23, an optional algorithm generates one or more scores for the stimulation set based on the frequency of use. The stimulation set, the patient frequency of use, and/or the score(s) may be stored in a searchable database [24]. Steps 15 and 25 are the same in both the general and specific methodologies: the database may be used at subsequent patient treatment. At step 26, the usage and scores for the associated stimulation sets may be updated based on subsequent patient use.

While the invention herein disclosed has been described in relation to pain therapies, it is not limited to such use. For example, patient feedback and satisfaction may be evaluated and stored for treatment of other conditions, such as, for example, peripheral vascular disease, congestive heart failure, angina, motor disorders, and urinary incontinence. For these other conditions, rating systems are known, such as, for example, Fontaine rating for peripheral vascular disease, the NYHA classifications for congestive heart failure and angina, the UPDRS, Hoehn and/or Yahr in motor disorders, and bladder capacity in urinary incontinence. As such, patient satisfaction based on any of these or other scales may be used to evaluate the electrical stimulation pulses delivered to the patient. As explained above, these evaluations may be stored and organized within a database associated with the stimulation sets. These scales may be incorporated into a suitable user interface, such as a touch screen as explained in relation to the VAS, in order to efficiently interpret patient feedback.

While the invention herein disclosed has been described by means of specific embodiments and applications thereof, numerous modifications and variations could be made thereto by those skilled in the art without departing from the scope of the invention set forth in the claims. For example, the methods discussed above are not limited to spinal cord stimulation systems and may be used with many kinds of stimulation systems such as, but not limited to, those described above, cochlear implants, cardiac stimulation systems, peripheral nerve stimulation systems, muscle tissue stimulation systems, brain stimulation systems and microstimulators.

What is claimed is:

1. A tissue stimulation system comprising:
    a pulse generating device for generating and outputting electrical stimulation pulses to at least one implantable electrode;
    a database for storing one or more stimulation sets that define parameters of the electrical stimulation pulses and for storing a frequency of use, patient feedback, and an overall score for each of the stimulation sets;
    a scale used for generating a score that is based on patient feedback and is inversely proportional to patient well-being;
    a computation device for calculating the overall score for each of the stimulation sets, the overall score being based on the frequency of use plus a highest possible score minus the score that is generated based on patient feedback; and
    a programmer for selecting one of the stimulation sets from the database based on the overall score and wherein the programmer is further configured for communicating with the pulse generating device in order to program the pulse generating device to generate the electrical stimulation pulses in accordance with the selected stimulation set.

2. The stimulation system of claim 1, wherein the scale comprises an interactive display screen, wherein the patient feedback is generated using an interactive display screen.

3. The stimulation system of claim 1, wherein the patient feedback is verbal patient comments.

4. The stimulation system of claim 1, wherein the patient feedback is based on objective criteria selected from the group consisting of perspiration, muscle tension, respiration rate, heart rate, and combinations thereof.

5. The stimulation system of claim 1, wherein the database is further configured for storing a level of patient satisfaction before and after the stimulation pulses are applied to the patient.

6. The stimulation system of claim 1, wherein the database is further configured for storing one or more of patient information, clinic information, and tissue stimulation device information.

7. The stimulation system of claim 1, wherein the computation device is for calculating the overall score for each of the stimulation sets based on the following equation:

$$\text{overall score}=(X\text{-}VAS)+(\text{use percentage}/10),$$

wherein VAS is a value from 1 to X representing the score that is generated based on patient feedback,
wherein X is a value representing the highest possible score, and
wherein the use percentage is a value representing the frequency of use for the stimulation set.

8. A method for evaluating and selecting at least one stimulation set, the method comprising:
    applying electrical stimulation pulses to the patient, wherein the electrical stimulation pulses are generated by a pulse generating device and are defined by a stimulation set;
    determining a level of pain after applying the electrical stimulation pulses based on a score obtained through patient feedback;
    determining a frequency of use for the stimulation set;
    calculating an overall score for the stimulation set, the overall score being based on the frequency of use plus a highest possible score minus the score that is obtained through patient feedback;
    retrievably storing the frequency of use, the patient feedback, the overall score, and the stimulation set in a database; and
    selecting the stimulation set based on the overall score.

9. The method of claim 8, further comprising updating the overall score based on subsequent patient feedback.

10. The method of claim 8, further comprising updating the database based on an updated frequency of use.

11. The method of claim 8, wherein determining the level of pain after applying the electrical stimulation pulses comprises using a visual analog scale to generate the score that is obtained through patient feedback.

12. The method of claim 8, further comprising calculating the overall score for the stimulation set based on the following equation:

$$\text{overall score}=(10\text{-}VAS)+(\text{use percentage}/10),$$

wherein VAS is a value from 1 to 10 representing the score that is obtained through patient feedback or a level of pain during application of the electrical stimulation pulses, and
wherein the use percentage is a value representing the frequency of use for the stimulation set.

13. The method of claim 8, wherein the overall score is calculated according to the following equation:

$$\text{overall score}=(X\text{-}VAS)+(\text{use percentage}/10),$$

wherein VAS is a value from 1 to X representing the score that is obtained through patient feedback,
wherein X is a value representing the highest possible score, and
wherein the use percentage is a value representing the frequency of use for the stimulation set.

14. The method of claim 8 further comprising:
applying a second ser of electrical stimulation pulses to the patient, wherein the second set of electrical stimulation pulses is defined by a second stimulation set;
determining a second level of pain after applying the second set of electrical stimulation pulses based on a second score obtained through a second patient feedback;
determining a second frequency of use for the second stimulation set;
calculating a second overall score for the second stimulation set, the second overall score being based on the second frequency of use plus the highest possible score minus the second score;
retrievably storing the second frequency of use, the second patient feedback, the second overall score, and the second stimulation set in the database; and selecting the second stimulation set based on the second overall score.

15. The method of claim 8, further comprising:
searching the database for at least one desired stimulation set for use in a future stimulation session.

16. The method of claim 15, wherein an overall score of the desired stimulation set is greater than a threshold value.

* * * * *

UNITED STATES PATENT AND TRADEMARK OFFICE
CERTIFICATE OF CORRECTION

PATENT NO. : 7,657,317 B2
APPLICATION NO. : 11/115789
DATED : February 2, 2010
INVENTOR(S) : Thacker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 597 days.

Signed and Sealed this

Thirtieth Day of November, 2010

David J. Kappos
*Director of the United States Patent and Trademark Office*